United States Patent
Donnelly et al.

(10) Patent No.: US 11,278,305 B2
(45) Date of Patent: *Mar. 22, 2022

(54) SELECTIVE TISSUE REMOVAL TREATMENT DEVICE

(71) Applicant: HYDROCISION, INC., North Billerica, MA (US)

(72) Inventors: Howard W. Donnelly, Needham, MA (US); Mark Lewis, Haverhill, MA (US); Lynne Messina, Cambridge, MA (US)

(73) Assignee: HYDROCISION, INC., North Billerica, MA (US)

(*) Notice: Subject to any disclaimer, the term of this patent is extended or adjusted under 35 U.S.C. 154(b) by 295 days.

This patent is subject to a terminal disclaimer.

(21) Appl. No.: 16/658,107

(22) Filed: Oct. 20, 2019

(65) Prior Publication Data

US 2020/0046397 A1 Feb. 13, 2020

Related U.S. Application Data

(63) Continuation of application No. 15/631,722, filed on Jun. 23, 2017, now Pat. No. 10,485,568.

(60) Provisional application No. 62/354,515, filed on Jun. 24, 2016.

(51) Int. Cl.
*A61B 17/32* (2006.01)
*A61B 17/3203* (2006.01)
*A61B 17/00* (2006.01)

(52) U.S. Cl.
CPC .. *A61B 17/320016* (2013.01); *A61B 17/3203* (2013.01); *A61B 17/00234* (2013.01); *A61B 2217/005* (2013.01)

(58) Field of Classification Search
CPC ........ A61B 17/3203; A61B 17/320092; A61B 17/320016; A61B 2217/005; A61M 5/1582

See application file for complete search history.

(56) References Cited

U.S. PATENT DOCUMENTS

| 1,889,425 A | 11/1932 | Sorensen |
| 1,902,418 A | 3/1933 | Pilgrim |
| 3,565,062 A | 2/1971 | Kuris |

(Continued)

FOREIGN PATENT DOCUMENTS

| DE | 4018736 A1 | 1/1992 |
| EP | 0551920 A1 | 7/1993 |

(Continued)

OTHER PUBLICATIONS

Huh et al., "Comparison of SpineJet XL and Conventional Instrumentation for Disk Space Preparation in Unilateral Transforaminal Lumbar Interbody Fusion". J Korean Neurosurg Soc. May 2010;47(5):370-6.

(Continued)

*Primary Examiner* — Tiffany Legette
(74) *Attorney, Agent, or Firm* — Bochner IP, PLLC; Andrew D. Bochner

(57) ABSTRACT

This disclosure describes techniques and devices for improvement of surgical outcomes for tissue removal surgeries. A surgical instrument with adjustable and selective resection is described. The disclosed devices and methods allow selective tissue removal.

18 Claims, 6 Drawing Sheets

(56) References Cited

U.S. PATENT DOCUMENTS

| | | |
|---|---|---|
| 3,590,813 A | 7/1971 | Roszyk |
| 3,818,913 A | 6/1974 | Wallach |
| 3,930,505 A | 1/1976 | Wallach |
| 3,965,901 A | 6/1976 | Penny et al. |
| 4,024,866 A | 5/1977 | Wallach |
| 4,111,490 A | 9/1978 | Liesveld |
| 4,137,804 A | 2/1979 | Gerber et al. |
| 4,282,867 A | 8/1981 | Du Toit |
| 4,368,734 A | 1/1983 | Banko |
| 4,435,902 A | 3/1984 | Mercer et al. |
| 4,560,373 A | 12/1985 | Sugino et al. |
| 4,690,672 A | 9/1987 | Veltrup |
| 4,694,828 A | 9/1987 | Eichenbaum |
| 4,705,500 A | 11/1987 | Reimels et al. |
| 4,715,848 A | 12/1987 | Beroza |
| 4,898,574 A | 2/1990 | Uchiyama et al. |
| 4,913,698 A | 4/1990 | Ito et al. |
| 4,935,006 A | 6/1990 | Hasson |
| 5,027,792 A | 7/1991 | Meyer |
| 5,037,431 A | 8/1991 | Summers et al. |
| 5,057,098 A | 10/1991 | Zelman |
| 5,135,482 A | 8/1992 | Neracher |
| 5,135,484 A | 8/1992 | Wright |
| 5,186,714 A | 2/1993 | Boudreault et al. |
| 5,195,958 A | 3/1993 | Phillips |
| 5,217,465 A | 6/1993 | Steppe |
| 5,230,704 A | 7/1993 | Moberg et al. |
| 5,242,449 A | 9/1993 | Zaleski |
| 5,250,065 A | 10/1993 | Clement et al. |
| 5,255,017 A | 10/1993 | Lam |
| 5,259,842 A | 11/1993 | Plechinger et al. |
| 5,300,022 A | 4/1994 | Klapper et al. |
| 5,318,518 A | 6/1994 | Plechinger et al. |
| 5,322,504 A | 6/1994 | Doherty et al. |
| 5,370,609 A | 12/1994 | Drasler et al. |
| 5,453,088 A | 9/1995 | Boudewijn et al. |
| 5,476,450 A | 12/1995 | Ruggio |
| 5,496,267 A | 3/1996 | Drasler et al. |
| 5,505,729 A | 4/1996 | Rau |
| 5,527,330 A | 6/1996 | Tovey |
| 5,551,448 A | 9/1996 | Matula et al. |
| 5,556,406 A | 9/1996 | Gordon et al. |
| 5,562,640 A | 10/1996 | McCabe et al. |
| 5,562,692 A | 10/1996 | Bair |
| 5,591,184 A | 1/1997 | McDonnell et al. |
| 5,607,391 A | 3/1997 | Klinger et al. |
| 5,620,414 A | 4/1997 | Campbell, Jr. |
| 5,667,480 A | 9/1997 | Knight et al. |
| 5,674,226 A | 10/1997 | Doherty et al. |
| 5,713,849 A | 2/1998 | Bosma et al. |
| 5,713,851 A | 2/1998 | Boudewijn et al. |
| 5,766,194 A | 6/1998 | Smith |
| 5,782,795 A | 7/1998 | Bays |
| 5,788,667 A | 8/1998 | Stoller |
| 5,853,384 A | 12/1998 | Bair |
| 5,871,462 A | 2/1999 | Yoder et al. |
| 5,908,403 A | 6/1999 | Bosma et al. |
| 5,944,686 A | 8/1999 | Patterson et al. |
| 5,947,988 A | 9/1999 | Smith |
| 6,066,150 A | 5/2000 | Gonon |
| 6,280,302 B1 | 8/2001 | Hashish et al. |
| 6,322,533 B1 | 11/2001 | Gonon |
| 6,375,635 B1 | 4/2002 | Moutafis et al. |
| 6,402,715 B2 | 6/2002 | Manhes |
| 6,451,017 B1 | 9/2002 | Moutafis et al. |
| 6,511,493 B1 | 1/2003 | Moutafis et al. |
| 6,669,710 B2 | 12/2003 | Moutafis et al. |
| 6,960,182 B2 | 11/2005 | Moutafis et al. |
| 7,122,017 B2 | 10/2006 | Moutafis et al. |
| 7,337,538 B2 | 3/2008 | Moutafis et al. |
| 7,431,711 B2 | 10/2008 | Moutafis et al. |
| 7,717,685 B2 | 5/2010 | Moutafis et al. |
| 8,062,246 B2 | 11/2011 | Moutafis et al. |
| 8,162,966 B2 | 4/2012 | Connor et al. |
| 8,574,186 B2 | 11/2013 | Fischer |
| 9,597,107 B2 | 5/2017 | Staid et al. |
| 2002/0050197 A1 | 5/2002 | Moutafis et al. |
| 2002/0111579 A1* | 8/2002 | Moutafis ............ A61B 17/3203 604/43 |
| 2002/0176788 A1 | 11/2002 | Moutafis et al. |
| 2004/0243157 A1 | 12/2004 | Connor et al. |
| 2006/0129086 A1 | 6/2006 | McRury et al. |
| 2006/0229550 A1 | 10/2006 | Staid et al. |
| 2006/0264808 A1 | 11/2006 | Staid et al. |
| 2007/0239085 A1 | 10/2007 | Fehre et al. |
| 2009/0306692 A1 | 12/2009 | Barrington et al. |
| 2010/0010524 A1 | 1/2010 | Barrington et al. |
| 2010/0331883 A1 | 12/2010 | Schmitz et al. |
| 2017/0312282 A1 | 11/2017 | Robinson et al. |
| 2017/0367724 A1 | 12/2017 | Donnelly et al. |

FOREIGN PATENT DOCUMENTS

| | | |
|---|---|---|
| WO | 1990/05493 A1 | 5/1990 |
| WO | 1996/24299 A1 | 8/1996 |
| WO | 1999/33510 A1 | 7/1999 |

OTHER PUBLICATIONS

Non-Final Office Action for U.S. Appl. No. 15/631,722, dated Feb. 21, 2019, 14 pages.

International Search Report and Written Opinion for Application No. PCT/US2017/039046, dated Sep. 26, 2017, 5 pages.

Non-Final Office Action for U.S. Appl. No. 15/937,415, dated Mar. 27, 2018, 26 pages.

* cited by examiner

SELECTIVE TISSUE REMOVAL TREATMENT DEVICE

This application claims priority under 35 USC § 119 to U.S. Provisional Application No. 62/354,515, which was filed on Jun. 24, 2016 and is herein incorporated by reference in its entirety.

BACKGROUND

The present disclosure relates to a surgical device for soft tissue treatment, including devices and methods for selectively cutting and removing tissues.

Tendon injuries are commonly caused by repeated tendon strain, and can range from simple micro tears with inflammation to complete tears and ruptures. Healthy tendons include mature, highly-organized, type I collagen fibers, which are capable of withstanding relatively large tensile loads. A typical tendon injury, or tendinopathy, may be marked by an increased presence of immature, type III collagen, characterized by a loose fibril organization. Increased type III collagen disrupts type I collagen alignment, potentially leading to a loss in strength and increased water retention of the tendon, which in turn, contributes to the cycle of injury and may lead to painful nerve impingement.

In order to treat tendon or other connective tissue injuries or diseases, minimally invasive devices and techniques for selectively removing soft tissues or portions of soft tissue, like type III collagen, while leaving healthy tissue undisturbed are desired. Conventional minimally invasive techniques may be performed using multiple instruments and entry points into the body. Such techniques may also require various compounds or equipment to enable visualization of a surgical site. A device that may reduce the number of entry points or instruments used, safely dislodge and remove pathologic tissue while leaving healthy, native tissues undisturbed, would provide significant advantages to surgeons and patients The present disclosure provides surgical devices and methods for selectively treating soft tissue.

BRIEF SUMMARY

In one embodiment, a surgical instrument includes a handle located at a proximal end of the surgical instrument adapted to be gripped by a user. The surgical instrument also includes a first lumen extending along a longitudinal axis of the surgical instrument from the proximal end to a distal end of the surgical instrument. An inner bore of the first lumen extends from an open proximal terminal end of the first lumen to a closed distal terminal end of the first lumen. The first lumen also includes a nozzle formed in a side wall proximate to the closed distal terminal end that is configured to enable a jet of fluid to exit the nozzle. The jet of fluid can selectively cut tissue and can provide a suction force to remove and/or evacuate tissue.

The surgical instrument additionally includes a second lumen extending adjacent to the first lumen with an inner bore of the second lumen extending from an open proximal terminal end of the second lumen to a closed distal terminal end of the second lumen. The inner bore of the second lumen has an inner diameter greater than an inner diameter of the first lumen. The second lumen also includes an aperture disposed opposite of the nozzle to receive therein the jet of fluid exiting the nozzle. When the surgical instrument is in operation a cutting and suction force is formed at the aperture of the second lumen to selectively remove a first tissue type from different tissue types located in a surgical site.

In another embodiment, a method of using a surgical instrument includes selecting a water jet cutting or suction force level on a surgical instrument to provide an adjustable cutting and suction force level; and inserting the surgical instrument into a surgical site. The method also includes creating the cutting and suction force with the surgical instrument within the surgical site by operation of the surgical instrument with the selected cutting and suction force level. The cutting and suction force is created by pumping a fluid through a nozzle of a first lumen of the surgical instrument into an aperture of a second lumen of the surgical instrument. The method further selectively cuts, a first tissue type from multiple (two or more) tissue types within the surgical site and evacuates, by the suction force, the cut first tissue type from the surgical site through the second lumen of the surgical instrument.

BRIEF DESCRIPTION OF THE DRAWINGS

The accompanying figures illustrate one or more embodiments of the invention. The drawings are not necessarily to scale. The present invention is illustrated by way of example, and not limitation, in the accompanying figures wherein.

DETAILED DESCRIPTION

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints. Multiple will be understood to refer to two or more.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Current minimally invasive surgical techniques may cause damage to tissues that are not targeted during a surgical procedure. The introduction of multiple entry points and introducing foreign visualization compounds to the body may create trauma that may prolong patient recovery times and increase the overall cost associated with non-invasive procedures. Current minimally invasive surgical techniques could be improved by enabling the selective removal of tissues from a surgical site. Therefore, there is a need for a method to effectively and safely remove pathologic tissues while minimizing trauma at a surgical site by using a single device, and/or to selectively remove types of tissue.

Embodiments of the present surgical instruments and methods allow for selective removal of tissue from a surgical site that limits the number of entry points and/or amount of foreign compound introduced into the body. In one embodiment, the surgical instrument is configured to create a cutting and suction force between a first lumen and second lumen. The cutting and suction force selectively removes a specified tissue type from the surgical site, and the level of force may be adjusted to target a certain soft tissue by setting the fluid pressure travelling through a first lumen. The removed tissue is evacuated with a moving fluid through the second lumen. As such the water jet results in a cutting force and suction force, thereby allowing cutting and removal of tissue with one device.

Figure 1:
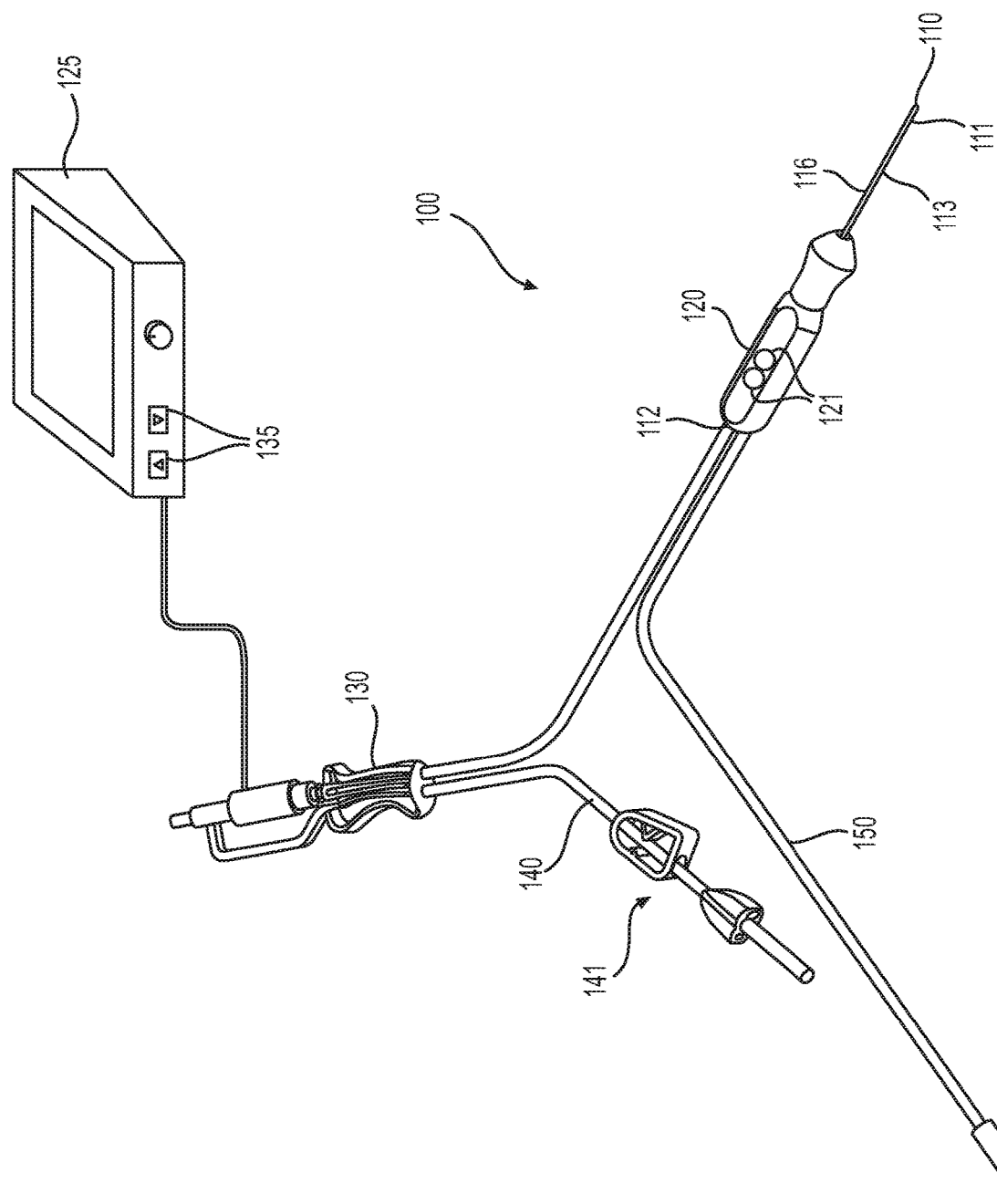
FIG. 1 is a perspective view of a surgical instrument according to an exemplary embodiment.

FIG. 1 is a perspective view of a surgical instrument 100 according to an exemplary embodiment. The surgical instrument 100 includes an insertion end 110 attached to a handle 120. The insertion end 110 includes a first lumen 113 and a second lumen 116 extending through or otherwise attached to the handle 120. The first lumen 113 and the second lumen 116 are depicted and described further in accord with FIGS. 2 and 3, respectively. The handle 120 and/or lumens are connected to a pump assembly 130. The pump assembly 130 provides a jet of fluid travelling distally along first lumen 113. When the jet of fluid travels from the first lumen 113 to the second lumen 116 at the distal end 111 of the insertion end 110, a cutting and suction force is generated, which can allow selective removal of tissue. The distal end 111 is depicted and described further in accordance with FIG. 5.

The term "lumen" as used herein will be understood to refer to a structure that includes a wall with an open passageway therethrough. Although lumen may otherwise refer to an opening or passage within a tube, it will be understood in the present disclosure to refer to the physical tube or structure itself, and the "first lumen" and "second lumen" will be understood to also include an "inner bore" as discussed below.

Further, although the first lumen 113 and second lumen 116 are illustrated as straight tubes or rod-like structures, other shapes may be used. For example, the lumens may be curved or angled to allow access to specific anatomic locations. As such, although being illustrated as straight structures, other configurations may be included.

A user may adjust the pressure of the jet of fluid with an adjustor 135. The jet of fluid is provided through a supply line 140. The jet force is used to cut or resect tissue in a surgical site. Further, the level of force, which can be set by the adjustor 135, can determine the type of tissue cut and removed within the surgical site. The cutting and removal of tissue is discussed with more detail below. Cut tissue is evacuated with a moving fluid at the insertion end 110, through the second lumen 116 and/or handle 120, to the evacuation lumen 150.

The pump assembly 130 may be any power source connectable to the open proximal terminal end of the first lumen 113 that is suitable to create the suction force at an aperture or opening 118 of the second lumen 116. The aperture or opening 118 is depicted and described further in accord with FIG. 3. The pump assembly 130 may be a pump cartridge, peristaltic pump, a configuration with a piston for pumping the jet of fluid through the surgical instrument 100, or any other pump suitable for generation of the jet. The piston may be powered by a transmission or any other suitable powering means. In one embodiment, the pump assembly 130 delivers a pressurized jet of fluid. In one embodiment, the jet of fluid is water. As an example, the pump assembly 130 may pump a fluid into the first lumen 113 to form the jet of fluid exiting a nozzle or opening 115. The nozzle or opening 115 is depicted and described further in accord with FIG. 2.

The supply line 140 may include an inlet line adapted to connect with a fluid source. In one embodiment, the supply line includes a spike or other connector (e.g., Luer, threaded, or other connector) to attach to a fluid source. In one embodiment, the fluid source is an IV bag of fluid. The supply line 140 may further include a line clamp 141 configured to stop flow of the fluid from the fluid source. The supply line 140 may be composed of high pressure tubing.

In some embodiments, the amount of cutting and suction force generated in the surgical instrument 100 may be controllable by a user of the surgical instrument. In one embodiment, the amount of cutting and suction force produced in the surgical instrument 100 may be controlled by the user of the surgical instrument through a console 125. The console 125 may be a computing device or a mechanical device. For example, a console 125 may include an adjustor 135 operable to control the pressure of the fluid provided to the first lumen 113. The pressure of fluid travelling through the first lumen 113 can affect or determine the amount of force generated between the first lumen 113 and second lumen 116.

In one embodiment, the adjustor 125 may be a keypad in digital or mechanical communication with the pump assembly 130 and able to send commands to the pump assembly 130. In another embodiment, the console 125 may be a user interface provided by a tablet or other computing device, and the adjustor 135 may be a user interface element displayed thereon that is operable to accept commands for controlling the pump assembly 130. It will be appreciated that in other embodiments, the adjustor 135 may be a mechanical device such as a clamp or similar device operable on the fluid line being provided to the surgical instrument 100 without the use of a console 125. The adjustor 135 is discussed further below.

Alternatively, in another embodiment, the surgical instrument 100 may be configured to operate with only a pre-determined amount of water jet force and the force in such a case may not be adjustable by a user of the surgical instrument. In addition, in other embodiments, a controller is placed elsewhere to enable more convenient access to a user. For example, in one embodiment, the handle 120 is equipped with controllers 121, which allow manual adjustment directly by a user (e.g., by controlling a valve or other mechanism within the device). Alternatively, or additionally, the instrument 100 can include other control mechanisms, e.g., foot pedals, to allow control without interruption of a procedure by the user holding the instrument 100.

Figure 2:
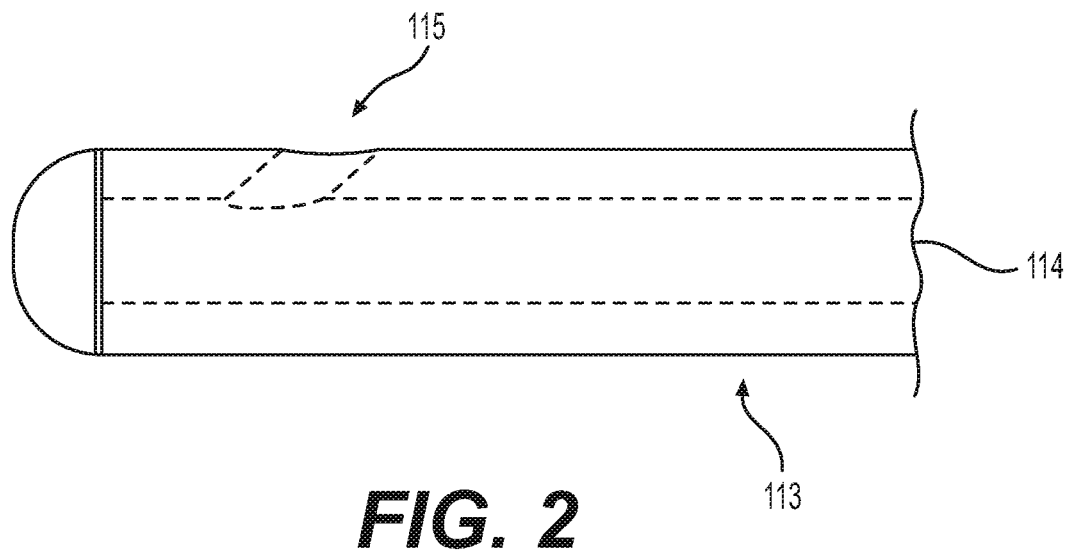
FIG. 2 is a side view with hidden lines visible of a first lumen of the surgical instrument according to an exemplary embodiment.

FIG. 2 is a side view with hidden lines visible of a first lumen 113 of the surgical instrument 100 according to an exemplary embodiment. The first lumen 113 extends along a longitudinal axis of the surgical instrument 100 from a proximal end 112 of the handle 120 to a distal end 111 of the surgical instrument 100. Inner bore 114 of the first lumen 113 extends from an open proximal terminal end of the first lumen 113 to a closed distal terminal end of the first lumen 113. The first lumen 113 guides fluid from the pump assembly 130 to the nozzle or opening 115. The nozzle or opening 115 is formed in a side wall proximate to the closed distal terminal end of the first lumen 113.

In some embodiments, the inner diameter of the first lumen 113 is 0.013 inches. In some embodiments, the diameter of the nozzle or opening 115 is 0.008 inches. In certain embodiments, the distal end of the nozzle or opening 115 is disposed 0.015 inches from the distal end of the first lumen 113, but variations may be made depending on the specific instrument size.

The open proximal terminal end of the first lumen 113 may be connectable to an energy source console. The energy source console is configurable to drive the surgical instrument 100 with an adjustable energy flow to adjust the cutting and suction force. In some embodiments, the energy source console includes the pump assembly 130, supply line 140, and the adjustor 135.

Figure 3:
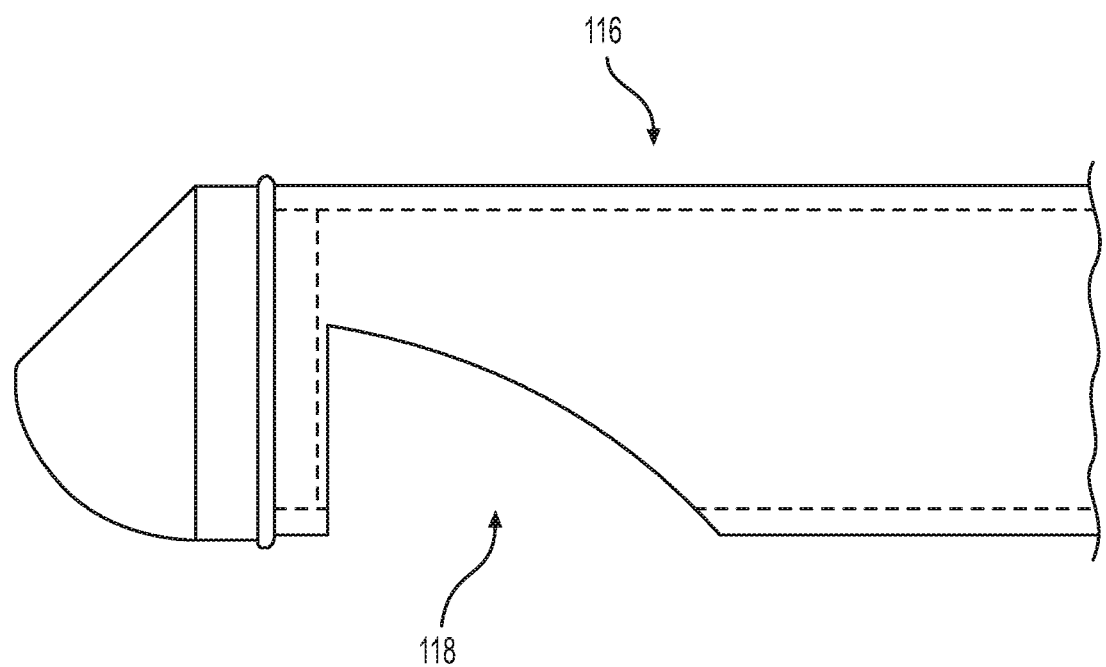
FIG. 3 is a side view with hidden lines visible of a second lumen of the surgical instrument according to an exemplary embodiment.

FIG. 3 is a side view with hidden lines visible of a second lumen 116 of the surgical instrument 100 according to an exemplary embodiment. The second lumen 116 includes an aperture or opening 118 configured to receive the jet of fluid travelling through nozzle or opening 115 of the first lumen 113.

In one embodiment, the inner diameter of the second lumen 116 is 0.05 inches. In another embodiment, the aperture or opening 118 is 0.065 inches in length. In another embodiment, the distal end of the aperture or opening 118 is disposed 0.081 inches from the distal end of the second lumen 116.

In one embodiment, the open proximal terminal end of the second lumen 116 is connectable to the evacuation lumen 150. In one embodiment, the second lumen 116 is connected to the evacuation lumen 150 through the handle 120, as depicted in FIG. 1. Tissue and fluid received by the second lumen 116 is transported to the evacuation lumen 150. In some embodiments, the evacuation lumen 150 is in communication with a receptacle for storing biological materials such as tissue and fluid.

Figure 4A:
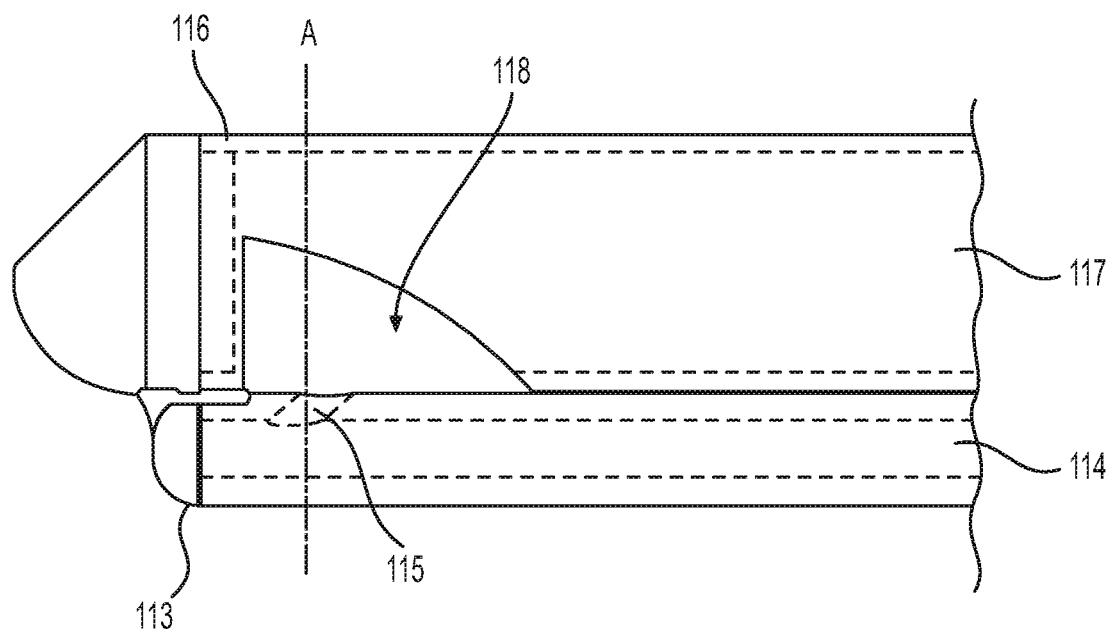
FIG. 4A is a side view with hidden lines visible of an assembled first lumen and second lumen of the surgical instrument according to an exemplary embodiment.

FIG. 4A is a side view with hidden lines visible of an assembled first lumen 113 and second lumen 116 of the surgical instrument 100 according to an exemplary embodiment. The second lumen 116 is disposed parallel to the first lumen 113 such that the aperture or opening 118 is disposed across from or otherwise aligned with the nozzle or opening 115 and configured to receive the jet of fluid. The second lumen 116 extends parallel to the first lumen 113 along the longitudinal axis of the surgical instrument 100, an inner bore 117 of the second lumen 116 extending from an open proximal terminal end of the second lumen 116 to a closed distal terminal end of the second lumen 116. The jet of fluid passing through nozzle 115 to aperture 118 enables the generation of a cutting and suction force. Creation of the cutting suction force is described in more detail below.

Figure 4B:
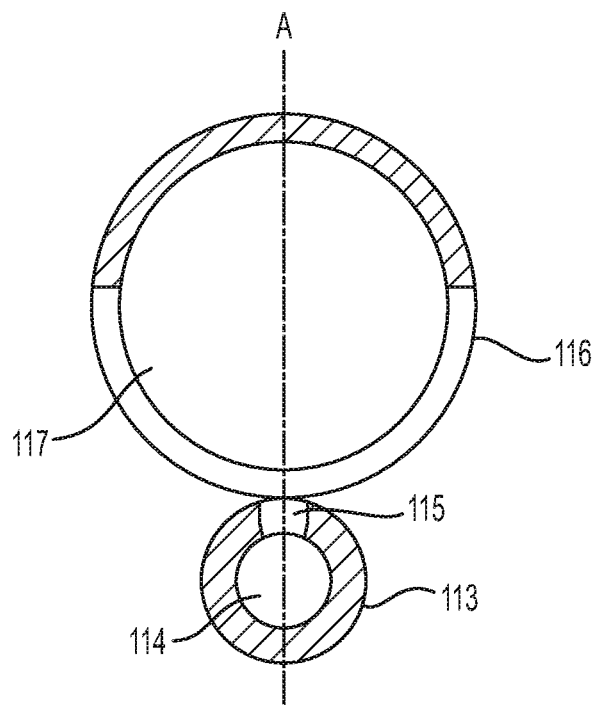
FIG. 4B is a cross-sectional view of an assembled first lumen and second lumen of the surgical instrument according to an exemplary embodiment.

FIG. 4B is a cross-section view of an assembled first lumen 113 and second lumen 116 of the surgical instrument 100 according to an exemplary embodiment. In some embodiments, the inner bore 117 of the second lumen 116 has an inner diameter greater than an inner diameter of the first lumen 113. In various embodiments, the width of nozzle or opening 115 is smaller than the width of the aperture or opening 118. In certain embodiments, the first lumen 113 is connected to the second lumen 116 by mechanical fixation, e.g., by welding, clamping, or forming as a unitary structure.

Figure 5:
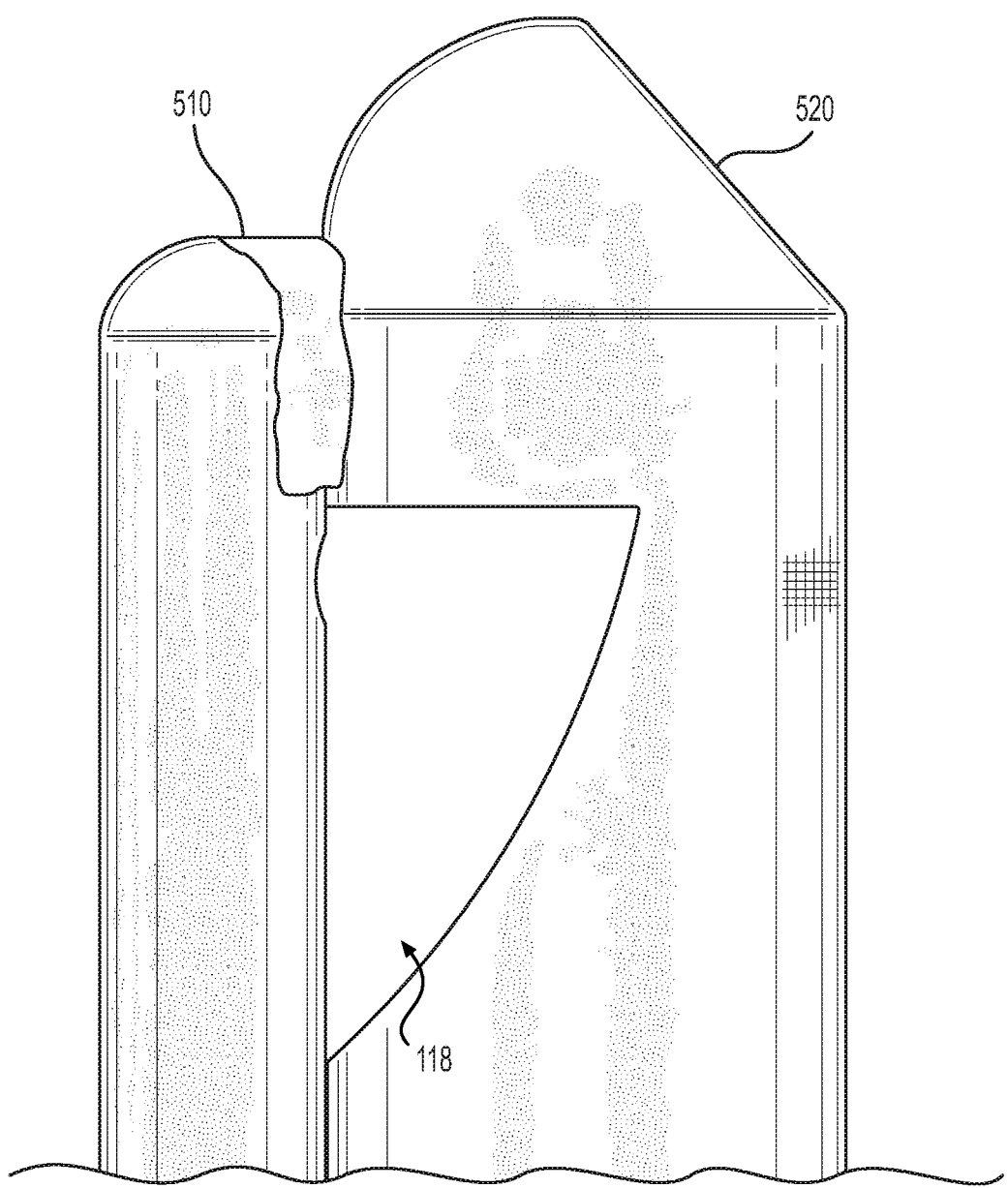
FIG. 5 is a side view of the distal end of the surgical instrument according to an exemplary embodiment.

FIG. 5 is a side view of the distal terminal end 111 of the surgical instrument 100 according to an exemplary embodiment. In one embodiment, distal terminal ends 510 and 520 of the first lumen 113 and the second lumen 116, respectively, are closed. In certain embodiments, the closed distal terminal end 510 of the first lumen 113 is shaped to assist moving the insertion end 110 through tissue of a patient. For example, the insertion end 110 may be inserted through dermal, fascial, muscular, adipose, or connective tissue (or any other anatomically reasonable tissue) to reach a surgical site. In one embodiment, the closed distal terminal end 520 of the second lumen 116 extends further than the closed distal terminal end of the first lumen 113. In an embodiment, the closed distal terminal end 520 of the second lumen 116 is pointed or beveled.

In one embodiment the insertion end 110 may be guided with the aid of ultrasound or other suitable imaging techniques. In an embodiment, ultrasound may be used to identify pathologic tissue in a joint or other structure without the aid of fluids. Pathologic tissue may be scar tissue, diseased tissue, dead tissue, inflamed tissue, or otherwise undesirable tissue. The insertion end 110 may be guided to the pathologic tissue to remove the identified tissue with a suction force. In an embodiment, the pathologic tissue is type III collagen.

In certain embodiments, diseased tissue or tissue otherwise desirable to remove is identified in an elbow joint or other musculo-skeletal structure. In some embodiments, the angle of the nozzle or opening 115, alignment of insertion end 110 and aperture or opening 118, with relation to second lumen 116 and the surgical site prevents dense tissue from being cut and removed by surgical instrument 100 because, in certain cases, it is too fibrous or is otherwise not as easily cut or removed as other tissue. For example, type I collagen has a highly aligned and densely packed structure, capable of withstanding high tensile forces. In contrast, type III collagen is less uniformly aligned and is not capable of withstanding large mechanical forces. As such, type III collagen may be removed at suction levels that may leave nearby type I collagen undisturbed.

In an embodiment, the surgical instrument 100 is suitable for use in different types of living tissue. In certain embodiments, the surgical instrument 100 is suitable for use in human tissue. In some embodiments, the surgical instrument 100 is suitable for use in joints or other musculo-skeletal structures.

In one embodiment, the surgical instrument 100 may be used to remove pathologic tissue from joints. In one example, the surgical instrument 100 may be used to remove pathologic tissue from tendons in elbow joints. The suction force can be adjusted to draw in or remove only selected tissue types, such as type III collagen or other tissue that is potentially pathologic, without disturbing other tissue types in the surgical site, such as type I collagen of healthy tendons. Specifically, different types of tissue withstand different thresholds of cutting and/or suction force, so by controlling the water jet force the types of tissue being removed from the surgical site can be controlled.

In some embodiments, the surgical instrument 100 may be utilized to remove pathologic tissue from different areas of the body, including without limitation, elbow, shoulder, knee, hip, ankle, or wrist joints. In one embodiment, the surgical instrument 100 may be utilized for removal of soft tissue in orthopedic procedures.

Figure 6:
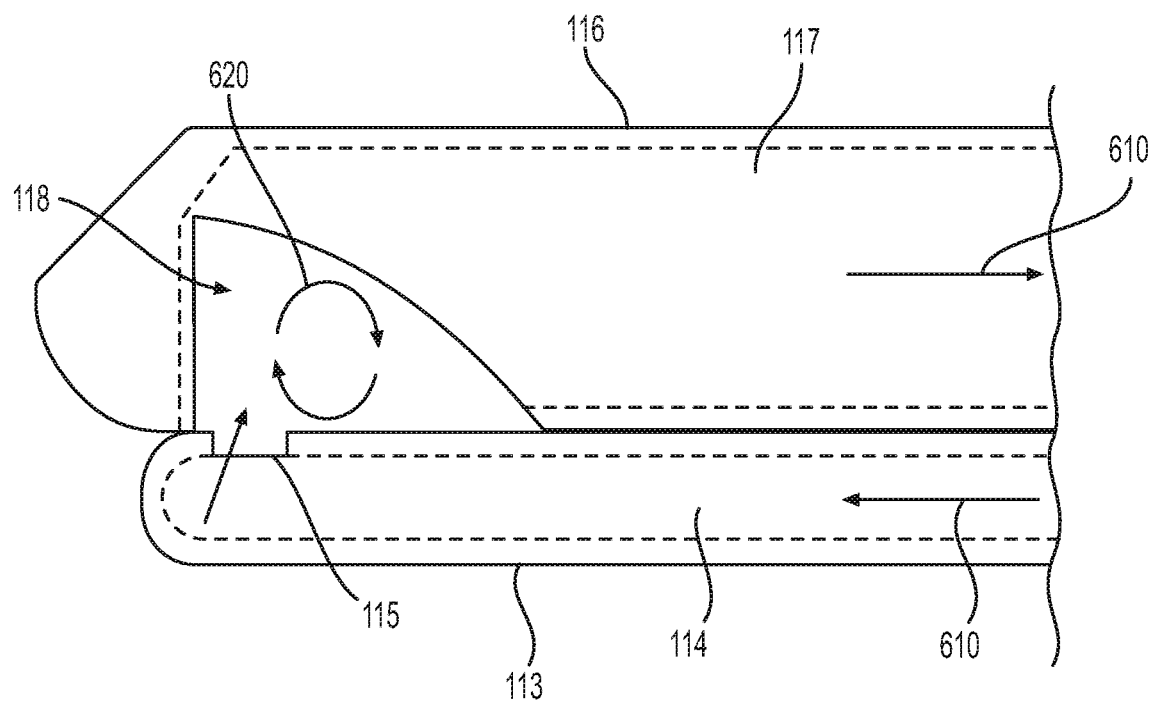
FIG. 6 is a side view with hidden lines visible of a jet of fluid traveling through the surgical instrument according to an exemplary embodiment.

FIG. 6 is a side view with hidden lines visible of a jet of fluid 610 traveling through the surgical instrument 100 according to an exemplary embodiment. The water jet force 620 is created when the jet of fluid 610 enters the aperture or opening 118 from the nozzle or opening 115. The jet of fluid 610 is a type of fluid capable of being pressurized and dispersed through the nozzle 115. In one embodiment, the fluid is water. In an embodiment, the jet of fluid 610 may leave the nozzle or opening 115 at a 55° angle relative to the opposing aperture or opening 118 of the second lumen 116 of the surgical instrument 100.

The jet of fluid 610 provided through supply line 140 may have a pressure set using the adjustor 135 and console 125 (or other control means) to produce an adequate cutting and/or suction at the distal end 111 to safely resect pathologic tissue. The pressure of the jet of fluid 610 can be about, more than about, or less than 100, 200, 400, 600, 800, 1,000, 2,000, 2,500, 3,000, 3,500, 4,000, 4,500, 5,000, 5,500, 6,000, 6,500, 7,000, 7,500, 8,000, 8,500, 9,000, 9,500, 10,000, 12,000, 14,000, 16,000, 18,000, or 20,000 psi. These values can be used to define a range, such as that from about 2,000 to about 14,000 psi, or from about 6,000 to 18,000 psi.

The cutting and/or suction force may be increased by increasing the pressure of the jet of fluid 610. As noted above, the pressure of the jet of fluid 610 may be increased or decreased by a user of the surgical instrument 100 via an adjustor 135. In one embodiment, the adjustor may be a manual tab for adjusting a power level of the surgical instrument 100, such as a wheel, knob, or lever. In some embodiments, the adjustor 135 has a fixed number of settings designating predetermined pressures for the jet of fluid 610. Table 1 illustrates exemplary pressure levels for water within the jet.

TABLE 1

Exemplary power levels and corresponding average pressures

| Power Level | Average Pressure (psi) |
| --- | --- |
| 1 | 2395 |
| 2 | 3574 |
| 3 | 4880 |
| 4 | 6244 |
| 5 | 7662 |
| 6 | 9078 |
| 7 | 10498 |
| 8 | 12020 |
| 9 | 13082 |
| 10 | 14065 |

In one embodiment, the pressure of the jet of fluid 610 pumped through the surgical instrument 100 ranges from 2,395 psi to 14,065 psi. In another embodiment, the pressure of the jet of fluid 610 ranges from 2,395 psi to 12,020 psi, or from 2,000 to 12,000 psi. It will be appreciated that other pressure ranges of greater and lesser values are also within the scope of the present invention.

The adjustor 135 (or other component) may include an adjustment means for adjusting the pressure of the jet of fluid through the pump assembly 130. The adjustment means may be at least one knob, button, lever, keypad, or any other suitable means for adjusting the pressure of the jet of fluid 610. In some embodiments, the adjustment means enables a user of the surgical instrument 100 to select a predetermined power level of pressure. In certain embodiments, the user can select one of ten power levels. In one embodiment, the surgical instrument 100 is configured to provide a predetermined pressure and does not include an adjustor.

Figure 7:
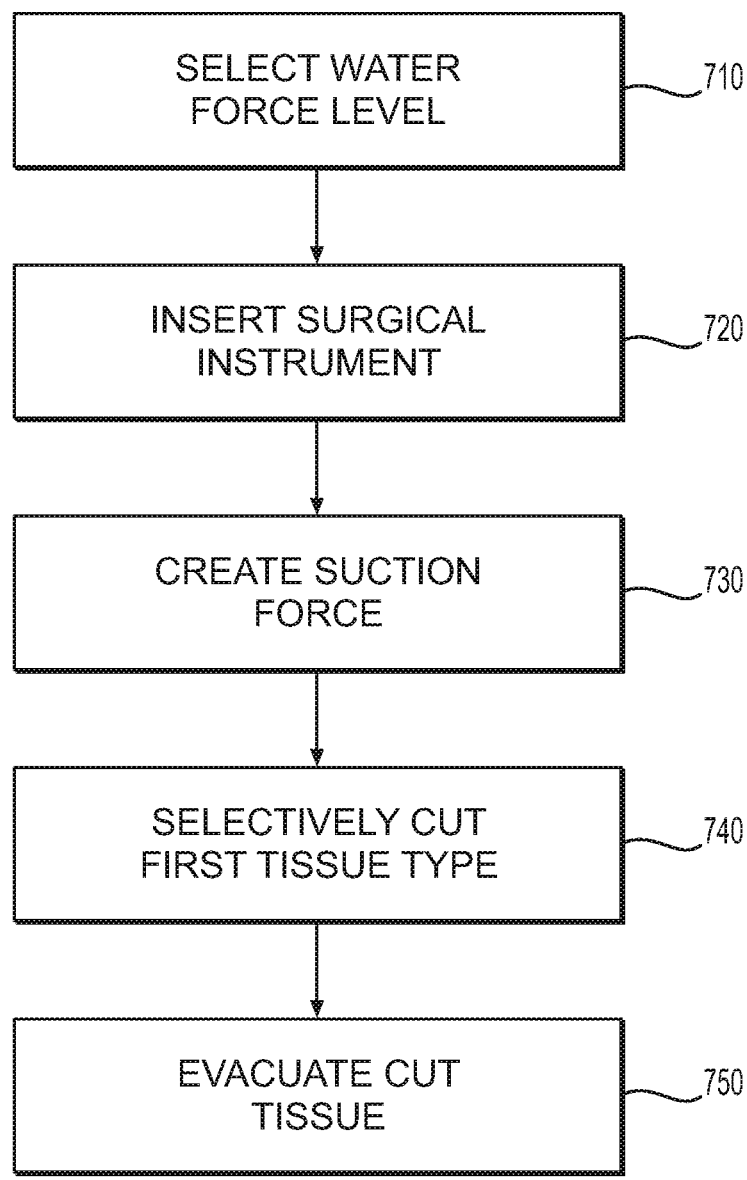
FIG. 7 is an exemplary sequence in a method of removing a selected tissue from a surgical site according to an exemplary embodiment.

FIG. 7 is a flowchart depicting an exemplary sequence in a method of removing a selected tissue from a surgical site according to an exemplary embodiment. The method begins after a surgical site is selected at Step 710 when a water force level is selected by a user of the surgical instrument. For example, the user may use an adjustor on the surgical instrument 100 to select a pre-determined power level. A suitable surgical site may be a joint in a patient. In one embodiment, the surgical site is an elbow joint. The water force level can be selected after at least a first tissue type is identified within the surgical site so that an appropriate suction force level is determined, or based on expected levels for known tissue types. The tissue type may be identified through ultrasound or other suitable imaging techniques, or by surgical experience or visual inspection. In some embodiments, multiple tissue types are identified.

At Step 720, a surgical instrument 100 is inserted into the surgical site. In one embodiment, an incision or puncture is made in a surgical site to allow insertion of the surgical instrument. In an embodiment, the surgical instrument 100 may be shaped to move through tissue of a patient. In another embodiment, a closed distal terminal end 520 of the second lumen 116 of the surgical instrument 100 is shaped to move through tissue of a patient.

At Step 730, a cutting and suction force is created within the surgical site using the surgical instrument 100 with the selected water force level. In one embodiment, the water force is created by pumping a fluid through the surgical instrument 100. In another embodiment, the water force is created by pumping a fluid through a nozzle or opening 115 of a first lumen 113 of the surgical instrument 100 into an aperture or opening 118 of a second lumen 116 of the surgical instrument 100. In an embodiment, the fluid is a jet of water 610. As described herein, in one embodiment, the pressure of the jet of water 610 may be adjusted to control the strength of the cutting or suction force.

At Step 740, the first tissue type is selectively cut or resected from the surgical site as a result of operation of the surgical instrument 100 with the selected cutting or suction force level. As an example, type III collagen can be removed from an elbow joint without removing type I collagen tissue by creating a cutting and/or suction force of sufficient strength to resect type III collagen without resecting type I collagen.

At Step 750, the cut or resected first tissue type is evacuated from the surgical site. In some embodiments, the cut or resected first tissue type is evacuated from the surgical site with fluid. In some embodiments, the cut or resected first tissue type and the fluid are evacuated through the second lumen 116 of the surgical instrument 110 to an evacuation lumen 150.

The tissue type(s) may be defined by a tissue density or other tissue property. For example, if a tendon or other tissue has been damaged or is diseased, the tendon may include more than one type of tissue, as the term "tissue type" should be presently understood. In one embodiment, the different tissue types may refer to healthy tissue and diseased tissue. In another embodiment, different tissue types may be identified by variations in tissue density (e.g., due to damage, disease, inflammation, etc). For example, if diseased or damaged tissue is to be removed from within or surrounding a tendon, different tissue types may include tendinous tissue or scar or damaged tissue surrounding or within the tendon, and the tissue types may have variations in density. For example, healthy tendon will be understood to have a first density while diseased tissue may have a second density, and as such, different tissues can be identified within a common anatomic structure (e.g., a single tendon), or in a separate structure (e.g., a tendon and surrounding or nearby scar). In some embodiments, a healthy tissue may have densities, for example, from 1,900 kg/m$^3$ to approximately 1,700 kg/m$^3$, while a second tissue type associated with the same tendon, but being damaged or diseased may have a density, for example, from 1,100 kg/m$^3$ to approximately 1,400 kg/m$^3$; 1,200 kg/m$^3$ to approximately 1,350 kg/m$^3$; or other ranges therebetween.

Certain types of tendinopathy may be treated using the disclosed devices and methods. For example, calcific tendinopathy of the shoulder, elbow, knee or other joints may be treated. Calcific tendinopathy can include damaged tendon with areas of weakness, which can also lead to significant morbidity due to pain associated with damaged tissue. Accordingly, removal of tissue affected by such conditions can be beneficial.

Since certain changes may be made without departing from the scope of the present invention, it is intended that all matter contained in the above description or shown in the accompanying drawings be interpreted as illustrative and not in a literal sense. Practitioners of the art will realize that the sequence of steps and architectures depicted in the figures may be altered without departing from the scope of the present invention and that the illustrations contained herein are singular examples of a multitude of possible depictions of the present invention.

The foregoing description of example embodiments of the invention provides illustration and description, but is not intended to be exhaustive or to limit the invention to the precise form disclosed. Modifications and variations are possible in light of the above teachings or may be acquired from practice of the invention. For example, while a series of acts has been described, the order of the acts may be modified in other implementations consistent with the principles of the invention. Further, non-dependent acts may be performed in parallel.

It should be appreciated that the various embodiments individually described herein may be practiced in combination in certain circumstances without departing from the scope of the present invention. Other embodiments will be apparent to those skilled in the art from consideration of the specification and practice of this disclosure. It is intended that the specification and examples be considered as exemplary only, with the true scope and spirit of the disclosed devices and methods being indicated by the following claims.

EXAMPLE

Tendinopathy Treatment Model

The following experiment demonstrates that the disclosed devices are capable of selectively removing collagen with different densities.

An in vitro study was performed to determine the ability of the disclosed device to remove pathologic tissue.

Initially, bovine flexor tendons from the ankle joint were harvested and characterized. Ultrasound was used to measure the density of the harvested tendon, which was measured to be approximately 1,900 kg/m$^3$. Tendons were separated into three groups, and subjected to injections of clostridial collagenase type 1 (290 units/mg, SIGMA-ALDRICH CORP.) in a dose escalation study from 1, 10, and 50 mg/ml. No collagenase was administered to a fourth, control group.

Following collagenase treatment, there was a significant decrease in tendon density in a dose-dependent manner. The tendon density of the 1 mg/ml group dropped from approximately 1,900 kg/m$^3$ to approximately 1,500 kg/m$^3$ after 24 hours. 72 hours after collagenase injection, the density further decreased to approximately 1,400 kg/m$^3$. The tendon group that was administered 50 mg/ml doses showed a similar pattern, resulting in complete degradation after 3 days.

The 1, 10, 50 mg/ml, and control groups were treated using the disclosed device and methods at various pressure settings. The untreated, control tendon group was resistant to debridement of tissue up to the highest pressure setting. Additionally, neither tissue injury nor removal of any kind occurred. The 1 mg/ml group demonstrated similar results when treated with the disclosed device. Minimal tissue removal was observed, until the highest settings were tested. Removal of low density tissue was observed when the 10 and 50 mg/ml collagenase dosage tendon groups were treated with the disclosed device. Particularly, removal of tissue with densities less than around 1,200 to 1,300 kg/m$^3$ was achieved.

The foregoing experiment indicated that the disclosed device was able to selectively resect tissues. Particularly, the disclosed device exhibited the capability to safely remove lower-density soft tissue while leaving higher-density soft tissue unperturbed.

What is claimed is:

1. A surgical instrument comprising:
   a handle for gripping;
   an insertion end comprising a first lumen and a second lumen, the first lumen and second lumen each comprising:
   a distal end, the distal end including a closed terminal end portion; and
   a proximal end attached to the handle;
   the first lumen extending along a longitudinal axis of the surgical instrument, the first lumen comprising:
   a first inner bore; and
   a nozzle formed in a side wall of the first lumen proximate to the closed terminal end portion, the nozzle configured to enable a jet of fluid to exit the nozzle; and
   the second lumen extending parallel to the first lumen along the longitudinal axis, the second lumen comprising:
   a second inner bore; and
   an aperture abutting and opposite the nozzle, the aperture configured to receive the jet of fluid therein,
   wherein the closed terminal end portion of the first lumen is located proximal to the closed terminal portion of the second lumen.

2. The surgical instrument of claim 1, wherein the fluid comprises water.

3. The surgical instrument of claim 1, wherein the closed terminal end of the second lumen is shaped to move through tissue of a patient.

4. The surgical instrument of claim 1, wherein the nozzle is 0.008 inches in diameter.

5. The surgical instrument of claim 1, wherein the aperture is 0.065 inches in length.

6. The surgical instrument of claim 1, wherein the surgical instrument is configured to create a cutting and suction force at the aperture of the second lumen, the suction force selectively drawing a first tissue type from a plurality of different tissue types located in a surgical site into the aperture and the cutting force cutting the first tissue type.

7. The surgical instrument of claim 1, wherein the second inner bore extends from an open proximal terminal end of the second lumen to the closed terminal end portion of the second lumen.

8. The surgical instrument of claim 1, wherein the second inner bore is greater in diameter than the first inner bore.

9. The surgical instrument of claim 1, wherein an open proximal terminal end is connectable to an energy source console.

10. The surgical instrument of claim 9, wherein the energy source console is configured to drive the surgical instrument with an adjustable energy flow to adjust a cutting and suction force.

11. The surgical instrument of claim 1, wherein a surgical site is a joint.

12. The surgical instrument of claim 11, wherein the surgical site is one of an elbow, shoulder, knee, hip, ankle, or wrist joint.

13. The surgical instrument of claim 12, wherein a first tissue type is pathologic tissue.

14. The surgical instrument of claim 1, further comprising a power source connectable to an open proximal terminal end of the first lumen.

15. The surgical instrument of claim 14, wherein the power source is a pump assembly configured to pump a fluid into the first lumen to form the jet of fluid exiting the nozzle.

16. The surgical instrument of claim 15, wherein the jet of fluid exiting the nozzle of the first lumen, entering into the aperture of the second lumen creates a cutting and suction force.

17. The surgical instrument of claim 16, wherein a pressure of the jet of fluid ranges from 2,395 psi to 14,065 psi.

18. The surgical instrument of claim 17, wherein the pressure of the jet of fluid ranges from 2,395 psi to 12,020 psi.

* * * * *